United States Patent [19]

Gerecht

[11] 4,048,338

[45] Sept. 13, 1977

[54] AQUEOUS COSMETIC COMPOSITION CONTAINING AMINE OXIDES

[75] Inventor: John Fred Gerecht, Somerville, N.J.

[73] Assignee: Colgate-Palmolive Company, New York, N.Y.

[21] Appl. No.: 613,370

[22] Filed: July 24, 1975

Related U.S. Application Data

[62] Division of Ser. No. 414,586, Nov. 9, 1973, Pat. No. 3,926,861, which is a division of Ser. No. 166,253, July 26, 1971, Pat. No. 3,809,659, which is a division of Ser. No. 677,723, Oct. 24, 1967, Pat. No. 3,637,682.

[51] Int. Cl.$^2$ ................................................ A61K 7/50
[52] U.S. Cl. .................................... 424/358; 8/10.1; 424/70
[58] Field of Search ................ 424/358, 365, 70; 8/10.1

[56] References Cited

U.S. PATENT DOCUMENTS

| | | | |
|---|---|---|---|
| 3,098,794 | 7/1963 | Dohr et al. | 8/10.1 |
| 3,449,430 | 6/1969 | Dohr et al. | 424/70 X |
| 3,470,102 | 9/1969 | Heinz | 424/70 |
| 3,533,955 | 10/1970 | Pader et al. | 424/70 |
| 3,637,682 | 1/1972 | Gerecht | 424/365 |
| 3,809,659 | 5/1974 | Gerecht | 252/542 |

*Primary Examiner*—Dale R. Ore
*Attorney, Agent, or Firm*—Richard N. Miller; Murray M. Grill; Herbert S. Sylvester

[57] ABSTRACT

Hydroxy higher alkyl morpholine oxides, and formulations containing the same. The compounds have many beneficial effects in detergent and cosmetic compositions, particularly desirable for application to the skin and for modification of foaming power of detergent compositions.

7 Claims, No Drawings

AQUEOUS COSMETIC COMPOSITION CONTAINING AMINE OXIDES

This is a divisional of application Ser. No. 414,586, filed Nov. 9, 1973, now U.S. Pat. No. 3,926,861, which is a divisional of application Ser. No. 166,253, filed July 26, 1971, now U.S. Pat. No. 3,809,659, which is a divisional of application Ser. No. 677,723, filed Oct. 24, 1967, now U.S. Pat. No. 3,637,682.

This invention relates to morpholine oxides.

One aspect of this relates to morpholine oxides of the formula

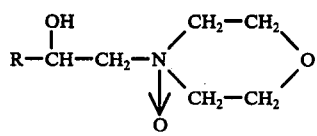

where R is a long chain alkyl group of at least 6 carbon atoms, e.g. 6 to 20, preferably 10 to 14, carbon atoms.

It has been found that the compounds of this invention have beneficial and unusual characteristics, particularly suitable, for example, in cosmetic and detergent applications.

The compounds described above may be prepared by reacting a long chain 1,2 epoxide with morpholine, followed by the conversion of the resulting N-2-hydroxyalkyl-morpholine to the corresponding N-oxide by oxidation, as with hydrogen peroxide.

Examples of 2-hydroxyalkyl groups are 2-hydroxydodecyl, 2-hydroxyoctadecyl, 2-hydroxynonyl, 2-hydroxydecyl, 2-hydroxyundecyl, 2-hydroxytridecyl, 2-hydroxytetradecyl, 2-hydroxypentadecyl, 2-hydroxyhexadcyl, and 2-hydroxyheptadecyl. Mixtures of compounds of different 2-hydroxyalkyl groups may be employed (e.g. a mixture in which these groups have 12–16 carbon atoms).

The compounds of this invention have many desirable attributes of particular value in emulsification and cleansing and detergency. Among these attributes are a desirable effect on the skin, and particularly a nonirritating and even anti-irritating effect when used in conjunction with surface active agents that ordinarily irritate the skin. The use of the compositions of the invention gives desirable modifications of the foaming power and/or foam characteristics of detergent compositions, such as a foam boosting effect. By using the new compounds valuable compositions intended for application to the skin or hair (or for use in contact with the skin) may be formulated. This invention also provides novel compounds of good miscibility with water which may be formulated into aqueous compositions which remain clear over a wide temperature range.

The novel compounds may be employed in detergent compositions, including light-duty liquids, heavy duty highly-built liquids, and granular compositions in which they may, for example, be post-added to spray-dried built detergent powders. In such detergent compositions they may be mixed with polymeric materials including agents for preventing redeposition of soil, such as sodium carboxymethylcellulose or polyvinyl alcohol; opacifiers, perfumes; anti-tarnishing agents; bacteriostatic agents; and oxygen- and chlorine-releasing bleaches. The novel compounds may also be used in hair-shampooing, hair-dyeing, or other hair-treating or hair-conditioning compositions. The novel compounds may be incorporated in a variety of cosmetic compositions, including such compositions intended for application to the skin as skin lotions, creams, gels, or clear liquids.

In the use of the novel hydroxyalkyl morpholine oxides of this invention in detergent compositions, the new compound may be used alone or may be added to any of the conventional surface-active detergents. These may be of the anionic, non-ionic, cationic or amphoteric types, or mixtures thereof.

The anionic surface active agents include those surface active or detergent compounds which contain an organic hydrophobic group and an anionic solubilizing group. Typical examples of anionic solubilizing groups are sulfonate, sulfate, carboxylate, phosphonate and phosphate. Examples of suitable anionic detergents which fall within the scope of the invention include the soaps, such as the water-soluble salts of higher fatty acids or rosin acids, such as may be derived from fats, oils and waxes of animal, vegetable or marine origin, e.g., the sodium soaps of tallow, grease, coconut oil, tall oil and mixtures thereof; and the sulfated and sulfonated synthetic detergents, particularly those having about 8 to 26, and preferably about 12 to 22, carbon atoms to the molecule.

As examples of suitable synthetic anionic detergents there may be cited the higher alkyl mononuclear aromatic sulfonates such as the higher alkyl benzene sulfonates containing from 10 to 16 carbon atoms in the alkyl group in a straight or branched chain, e.g., the sodium salts of higher alkyl benzene sulfonates or of the hgher alkyl toluene, xylene and phenol sulfonates; alkyl naphthalene sulfonate, ammonium diamyl naphthalene sulfonate, and sodium dinonyl naphthalene sulfonate. In one preferred type of composition there is used a linar alkyl benzene sulfonate having a high content of 3- (or higher) phenyl isomers and a correspondingly low content (well below 50%) of 2- (or lower) phenyl isomers; in other terminology, the benzene ring is preferably attached in large part at the 3 or higher (e.g. 4, 5, 6 or 7) position of the alkyl group and the content of isomers in which the benzene ring is attached at the 2 or 1 position is correspondingly low. Particularly preferred materials are set forth in U.S. Pat. No. 3,320, 174, May 16, 1967, of J. Rubinfeld.

Other anionic detergents are the olefin sulfonates, including long chain alkene sulfonates, long chain alkene sulfonates, long chain hydroxyalkane sulfonates or mixtures of alkane sulfonates and hydroxyalkane sulfonates. These olefin sulfonate detergents may be prepared, in known manner, by the reaction of $SO_3$ with long chain olefins (of 8–25, preferably 12–21 carbon atoms) of the formula $RCH=CHR_1$, where R is alkyl and $R_1$ is alkyl or hydrogen, to produce a mixture of sultones and alkenesulfonic acids, which mixture is then treated to convert the sultones to sulfonates. Examples of other sulfate or sulfonate detergents are paraffin sulfonates, such as the reaction products of alpha olefins and bisulfites (e.g. sodium bisulfite), e.g. primary paraffin sulfonates of about 10–20, preferably about 15–20, carbon atoms; sulfates of higher alcohols; salts of α-sulfofatty esters (e.g. of about 10- to 20 carbon atoms, such as methyl α-sulfomyristate or α-sulfotallowate).

Examples of sulfates of higher alcohols are sodium lauryl sulfate, sodium tallow alcohol sulfate. Turkey Red Oil or other sulfated oils, or sulfates of mono- or di-glycerides of fatty acids (e.g. stearic monoglyceride monosulfate), alkyl poly (ethenoxy) ether sulfates such as the sulfates of the condensation products of ethylene oxide and lauryl alcohol (usually having 1 to 5 ethenoxy groups per molecule); lauryl or other higher alkyl glyceryl ether sulfonates; aromatic poly (ethenoxy) ether sulfonates such as the sulfates of the condensation products of ethylene oxide and nonyl phenyl (usually having 1 to 6 oxyethylene groups per molecule).

The suitable anionic detergents include also the acyl sacosinates (e.g. sodium lauroylsarcosinate) the acyl esters (e.g. oleic acid ester) of isethionates, and the acyl N-methyl taurides (e.g. potassium N-methyl lauroyl- or oleyl tauride).

The most highly preferred water soluble anionic detergent compounds are the ammonium and substituted ammonium (such as mono-, di- and triethanolamine), alkali metal (such as sodium and potassium) and alkaline earth metal (such as calcium and magnesium) salts of the higher alkyl benzene sulfonates, olefin sulfonates, the higher alkyl sulfates, and the higher fatty acid monoglyceride sulfates. The particular salt will be suitably selected depending upon the particular formulation and the proportions therein.

Nonionic surface active agents include those surface active or detergent compounds which contain an organic hydrophobic group and a hydrophilic group which is a reaction product of a solubilizing group such as carboxylate, hydroxyl, amido or amino with ethylene oxide or with the polyhydration product thereof, polyethylene glycol.

As examples of nonionic surfaces active agents which may be used there may be noted the condensation products of alkyl phenols with ethylene oxide, e.g., the reaction product of isooctyl phenyl with about 6 to 30 ethylene oxide units; condensation products of alkyl thiohenols with 10 to 15 ethylene oxide units; condensation products of higher fatty alchols such as tridecyl alcohol with ethylene oxide; ethylene oxide addends of monoesters of hexahydric alcohols and inner ethers thereof such as sorbitan monolaurate, sorbitol monooleate and mannitan monopalmitate, and the condensation products of polypropylene glycol with ethylene oxide.

Cationic surface active agents may also be employed. Such agents are those surface active detergent compounds which contain an organic hydrophobic group and a cationic solubilizing group. Typical cationic solubilizing groups are amine and quaternary groups.

As examples of suitable synthetic cationic detergents there may be noted the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amide-linked amines such as those of the type $R^1CONHC_2H_4NH_2$ wherein $R^1$ is an alkyl group of about 9 to 20 carbon atoms, such as N-2-amino ethyl-stearyl amide and N-amino ethyl myristyl amide; quaternary ammonium compounds wherein typically one of the groups linked to the nitrogen atom is an alkyl group of about 12 to 18 carbon atoms and three of the groups linked to the nitrogen atom are alkyl groups which contain 1 to 3 carbon atoms, including such 1 to 3 carbon alkyl groups bearing inert substituents, such as phenyl groups, and there is present an anion such as halogen, acetate, methosulfate, etc. Typical quaternary ammonium detergents are ethyl-dimethylstearyl ammonium cloride, benzyl-dimethyl-stearyl ammonium chloride, benzyl-dimethyl-stearyl ammonium chloride, trimethyl stearyl ammonium chloride, trimethyl-cetyl ammonium bromide, dimethyl-ethyl dilauryl ammonium chloride, dimethyl-propyl-myristyl ammonium chloride, and the corresponding methosulfates and acetates.

Examples of suitable amphoteric detergents are those containing both an anionic and a cationic group and a hydrophobic organic group, which is advantageously a higher aliphatic radical, e.g. of 10–20 carbon atoms. Among these are the N-long chain alkyl aminocarboxylic acids

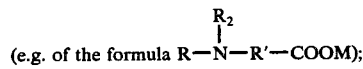

(e.g. of the formula R—N—R'—COOM);

the N-long chain alkyl iminodicarboxylic acids (e.g. of the formula $RN(R'COOM)_2$) and the N-long chain alkyl betains (e.g. of the

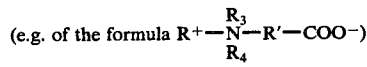

(e.g. of the formula $R^+$—N—R'—COO$^-$)

where R is a long chain alkyl group, e.g. of about 10–20 carbons, R' is a divalent radical joining the amino and carboxyl portions of an amino acid (e.g. an alklene radical of 1–4 carbon atoms), M is hydrogen or a salt-forming metal, $R^2$ is a hydrogen or another monovalent substituent) (e.g. methyl or other lower alkyl), and $R^3$ and $R^4$ are monovalent substituents joined to the nitrogen by carbon-to-nitrogen bonds (e.g. methyl or lower alkyl substituents). Examples of specific amphoteric detergents are N-alkyl-betaaminopropionic acid; N-alkyl-beta-iminodipropionic acid, and N-alkyl, N,N-dimethyl glycine; the alkyl group may be, for example, that derived from coco fatty alcohol, lauryl alcohol, myristyl alcohol (or a lauryl-myristyl mixture), hydrogenated tallow alcohol, cetyl, stearyl, or blends of such alcohols. The substituted aminopropionic and iminodiprionic acids are often supplied in the sodium or other salt forms, which may likewise be used in the practice of this invention. Examples of other amphoteric detergents are the fatty imidazolines such as those made by reacting a long chain fatty acid (e.g. of 10 to 20 carbon atoms) with diethylene triamine and monohalocarboxylic acids having 2 to 6 carbon atoms, e.g. 1-coco-5-hydroxethyl-5-carboxymethylimidazoline; betaines containing a sulfonic group instead of the carboxylic group; betains in which the long chain substituent is joined to the carboxylic group without an intervening nitrogen atom, e.g. inner salts of 2-trimethylamino fatty acids such as 2-trimethylaminolauric acid, and compounds of any of the previously mentioned types but in which the nitrogen atom is replaced by phosphorus.

The relative proportions of the hydroxyalkyl morpholine oxide and the other detergent may vary widely, e.g. in the range of ratios of 100:1 to 1:100; preferably about 5 to 30 parts of the morpholine oxide per 100 parts of the other detergent are used.

A very suitable dishwashing liquid detergent may contain, for example, a mixture of a linear higher alkylbenzene sulfonate and a higher alkyl ether sulfate in a ratio of about 0.4:1 to 1:1. In one type of sulfate-alkylbenzenesulfonate highly effective for this purpose, the alkylphenyl moiety has a molecule weight of 230 to 240; its alkyl group is largely (at least 80 mol percent) in the C10 to C12 range, at least half of the alkyls in the C10–C12 range being C10 and C11, The C10 and C11 being at least 45% of the total alkyl, at least 80% of the alkyl substituent being alkyl groups having the benzene attachment on the 3-(or higher, e.g. 3-4-5- or 6-) carbon of the alkyl. The higher alkyl ether sulfate in this dishwashing formulation may, for example, have the formula $R(OCH_2CH_2)_nSO_4M$ where R is long chain alkyl of 10 to 15 carbon atoms, n is about 1 to 5 (e.g. about 3) and M is a cation such as ammonium, sodium, potassium, mono- di- or triethanolammonium, etc.

Water-soluble builder salts may also be present, in the usual proportions, in the detergent formulations when heavy duty cleaning is desired. These salts include phosphates and particularly condensed phosphates (e.g. pyrophosphates or tripolyphosphates), silicates, borates and carbonates (including bicarbonates), as well as organic builders such as salts of nitrilotriacetic acid or ethylene diamine tetracetic acid. Sodium and potassium salts are preferred. Specific examples are sodium tripolyphosphates, potassium pyrophosphate, sodium hexametaphosphate, sodium carbonate, sodium bicarbonate, sodium sesquicarbonate, sodium tetraborate, sodium silicate, salts (e.g. Na salt) of methylene diphosphonic acid, trisodium nitrilotriacetate, of methylene diphosphonic acid, trisodium nitrilotriacetate, or mixtures of such builders, including mixtures of pentasodium tripolyphosphate and trisodium nitrilotriacetate in a ratio, of these two builders, of 1:10 to 10:1, e.g. 1:1. The proportions of builder salt may be, for example, 50 parts or more (e.g. 50 to 1000 parts) per 100 parts of detergent. A granular heavy duty detergent composition for washing clothes may comprise, for example, about 15-18% linear tridecylbenzenesulfonate of the type disclosed in Rubinfeld U.S. Pat. No. 3,320,174 May 16, 1967, about 20-50% hydrated pentasodium tripolyphosphate, about 3 to 8% sodium silicate, about 2-5% of the N-2-hydroxydodecyl morpholine oxide, and the balance sodium sulfate. A heavy duty detergent liquid composition for washing clothes in cool water may comprise, for example, an aqueous solution containing about 10% of a non-ionic detergent, about 25% of tetrapotassium pyrophosphate, about 1-7% of the N-hydroxyalkyl morpholine oxide and about 4% sodium silicate. Optical brighteners and soil-suspending agents may be included in the usual minor amounts in each case.

In formulating the novel hydroxyalkyl morpholine oxides of this invention into skin lotions, the new compound may be incorporated into the well known hand lotions containing water-immiscible materials such as mineral oils, blends of liquid mineral oils with high boiling petroleum fractions (such as paraffin wax, petrolatum or oxocerite), lanolin, fatty oil esters such as glyceryl monostearate, and fatty acids such as stearic or oleic acid. These water-immiscible materials may be components of an oil phase of an oil-in-water emulsion. A blend of about 1-3 parts of mineral oil, about 0.5-2 parts of either lanolin or lanolin alcohol or a mixture of these, about 1-3 parts of fatty acid and about 2-7 parts of polyhydroxy compound such as glyceryl monostearate may be used as the oil phase. The ratio of aqueous phase to oil phase is typically about 5:1 to 20:1. The aqueous phase may contain a detergent surfactant, for example in concentration of about 0.1 to 5% of said phase. The amount of the N-hydroxyalkyl morpholine oxide in the lotion may be, for example, in the range of about 0.2-5%.

In a typical method for making the lotion comprising an oil-in-water emulsion, the oil phase and water phase are heated (e.g. to 70°-80° C., say 74° C.) and the oil phase is added to the water phase and mixed thoroughly. The temperature is then lowered (e.g. to 35°-50° C., say 40° C.) and additional ingredients such as glycerine and calcium caseinate or other hydrophilic colloid are incorporated into the water phase of the emulsion.

The novel hydroxyalkyl morpholine oxides of this invention may be used in shampoo compositions in which they may be blended with any suitable water-soluble anionic detergent, which may be one of the well known types used in shampoos, e.g. an alkyl sulfate of for example, 12-18 carbon atoms, such as sodium lauryl sulfate or sodium tallow alcohol sulfate other sulfate detergents such as the triethanolammonium salt of the monosulfate of an ethoxylated lauryl alcohol (made from, for example, 3 mols of ethylene oxide and one mol of coconut alcohol), or a sulfonated detergent, such as an alkylbenzenesulfonate or olefin sulfonate or an amphoteric detergent such as an N-long chain alkyl aminocarboxylic acid or a N-long chain alkyl iminocarboxylic acid, as previously described herein. A typical shampoo composition may comprise, for example, an aqueous mixture containing about 1 to 15% of the hydroxyalkyl morpholine oxide and about 10 to 30% of the other detergent, and may be in free flowing liquid, cream, or lotion form.

The novel hydoxyalkyl morpholine oxides of this invention may also be used as constituents of toilet bars, in admixture with conventional toilet soaps, such as the usual sodium soap of a mixture of about 3 parts of tallow fatty acids and one part of coconut oil fatty acids, or in admixture with synthetic detergents such as the olefin sulfonates mentioned above or the long chain fatty acid (e.g. coconut oil fatty acid) monoglyercyl sulfates. In one example, about 15 parts of the hydroxyalkyl morpholine is used with 100 parts of the other detergent (soap or synthetic).

The following Examples are given to illustrate this invention further. In these examples, as in the remainder of the application, all proportions are by weight unless otherwise indicated.

EXAMPLE 1

20 grams of 1,2-epoxydodecene (b.p. 97°-98° C. at 3.5 mm Hg A) is heated with 9.7 grams of morpholine at 100° C. in a sealed container for 16 hours. The resulting mixture is then fractionally distilled and the product is collected at a temperature of 119° C. and a pressure of 0.05 mm Hg A. 23.4 grams of N-2-hydroxydodecyl-morpholine having an equivalent weight of 273, by titration (as compared to the calculated equivalent weight of 271 for this compound) are obtained. This product (23.4 grams) is mixed with 9.74 grams of aqueous 30% hydrogen peroxide and 50 ml of methanol and heated at 50° C. for 2 hours. Thereafter any excess peroxide is decomposed by adding 0.1 gram platinum black on charcoal (of 5% Pt content) and heating the mixture at 40° C. for 4 hours. The platinum-on-charcoal catalyst is filtered off, and the filtrate is evaporated to recover the crude product, which is then recrystallized from 300 ml of acetone to produce 17.5 grams of purified N-2-hydroxydodecyl-morpholine N-oxide having a melting point of 151°-2° C. (and having an equivalent weight by potentiometric titration in methanol, equivalence point at pH 3.25, of 290; as compared to the calculated equivalent weight of 287 for this compound).

EXAMPLE 2

A mixture of C12-C16 alpha olefins is epoxidized in conventional manner to give a mixture of 1,2-epoxyalkanes of 12-16 carbon atoms having an average molecular weight of about 207. 100 grams (0.48 mol) of this epoxide mixture is heated with 46 grams (a 10% excess) of morpholine in a Parr bomb having a magnetically operated stirrer, and maintained at a temperature of 100° C. overnight. The product is then distilled at a subatmospheric pressure (1 m Hg A) and the fractions distilling at 145°-185° C. (temperature of distilling head) are collected. The collected material is reacted with hydrogen peroxide as in Example 1, to produce a white solid mixture of N-2-hydroxyalkyl-morpholine oxides containing 12 to 16 carbons in the alkyl group.

EXAMPLE 3

Using the method described in Example 1, there is prepared N-2-hydroxyoctacecyl-morpholine oxide of melting point 147°-148° C. The measured equivalent weight is 371.5; the equivalent weight calculated for this compound is 371.6.

EXAMPLE 4

Tests of the foaming power of the compound of Example 1 are made by shaking cylinders containing the following solutions:
a. a 0.05% solution of the compound in water;
b. a solution of 0.05% of sodium linear alkylbenzenesulfonate detergent in water.
c. a solution of 0.05% of the compound and 0.05% of the foregoing alkylbenzenesulfonate in water. It is found that solution (b) foams much better than solution (a); and solution (c) yields more foam that solution (b) and the foam is more stable.

EXAMPLE 5

The N-2-hydroxydodecyl-morpholine N-oxide is tested for its effectiveness in reducing the skin irritation ordinarily caused by exposure to aqueous sodium lauryl sulfate. In this test there is used a control composition containing 2% of sodium lauryl sulfate in water, and an otherwise identical composition containing, in addition, 0.5% of the hydroxyalkylmorpholine oxide. Each composition is applied to the skin of rabbits twice a day for 2 days, using six different skin sites for each composition, and observing the irritation 48 hours after the beginning of the test. The composition containing the N-2hydroxydodecylmorpholine N-oxide is found to cause appreciably less skin irritation.

EXAMPLE 6

A hand lotion is formulated from the following ingredients:
a. an aqueous mixture of 74.4 parts deionized water, 1 part sodium lauryl sulfate, 1 part of the hydroxyalkyl morpholine oxide of Example 1, and, as preservatives, 0.18 part methyl p-hydroxybenzoate and 0.22 part propyl p-hydroxybenzoate.
b. a mixture of 2.0 parts light mineral oil, 5.0 parts glyceryl monostearate, 1.0 part lanolin alcohol (Amerchol H9) and 1.5 part stearic acid (triple pressed).
c. a mixture of 3.0 parts glycerin, 0.5 part calcium caseinate and 5.0 parts deionized water.
d. a mixture of 1 part benzyl alcohol and 0.5 part perfume.

The oily mixture (b) is melted and added to the aqueous mixture (a) while the latter is in heated agitated condition, to form an emulsion, which is allowed to cool. To the resulting warm mixture the glycerin-caseinate-water blend (c) is added, with stirring, and after further cooling, to room temperature, the benzylalcohol-perfume mixture (d) is added. The presence of the benzylalcohol helps to control the viscosity of the lotion.

In tests of the protective effect of the lotion against irritation by prolonged contact with an irritating detergent solution (aqueous sodium lauryl sulfate), the lotion of this Example is found to give improved protection as compared to a similar hand lotion free of the hydroxyalkyl morpholine oxide.

EXAMPLE 7

A liquid detergent composition is formulated from the following ingredients: sodium linear alkylbenzenesulfonate, 22%, ammonium salt of monosulfonate of ethoxylated sulfated straight chain primary alkanol (the alkanol having 12-14 carbon atoms and the ethoxylated product containing 3 ethylene oxide units per molecule), 10% ; mixed lauric/myristic (70/30) ethanolmide, 5%; N-2-hydroxydodecyl-morpholine oxide, 5%; ethanol, 5..3% sodium xylene sulfonate, 5.8%; and water, constituting substantially the remainder of the composition. A given amount of this detergent formulation is found to be effective for washing a considerably greater number of greased plates (36 vs. 27, in hard water) than an equal amount of an otherwise identical detergent formulation free of hydroxyalkyl morpholine oxide.

The alkylbenzenesulfonate is produced by sulfonation of an alkylbenzene of molecular weight 238, containing mainly alkyl groups of 10 to 12 carbons.

EXAMPLE 8

Example 7 is repeated except that the fatty acid monoethanolamide is omitted from the composition. The resulting detergent composition is found to be effective for washing a considerably greater number of greased plates (33 plates) than otherwise identical formulations containing (a) the fatty acid monoethanolamide in place of the hydroxyalkyl morpholine oxide (27 plates); (b) lauryl dimethylamine oxide in place of the hydroxyalkyl morpholine oxide (25 plates).

EXAMPLE 9

A liquid detergent composition is formulated from: the alkylbenzenesulfonate of Example 7, 35%; the ammonium alkyl ether sulfate of Example 7, 4%; N-2-hydroxydocecylmorpholine oxide, 5%; ethanol, 5.1%; urea, 5%; sodium xylenesulfonate, 1.7%. The resulting formulation is found to be effective for washing a considerably greater number of greased plates (39, in hard water) than an othewise identical formulation containing lauryl dimethylamine oxide in place of the hydroxyalkyl morpholine oxide (30 plates).

EXAMPLE 10

In another variation of the method of preparation of the novel compounds, one mol of the 1,2-epoxyalkane (e.g. 1,2-epoxydodecane) is reacted with 1.5 mols of morpholine under reflux at atmospheric pressure for 4 hours until all the epoxide has reacted. The excess of morpholine is then distilled off under vacuum, the reaction product is cooled to 50° CC., and 1.05 mols of aqueous 35% hydrogen peroxide are added slowly while the mixture is stirred and cooled to maintain its temperature below 85° C. Toward the end of the reaction the mixture is diluted with water so that it can still be stirred readily. The mixture is then heated to 85°–90° C. for 1 hour. When 1,2-epoxy dodecane is used as the starting material, there is obtained a slightly yellow solution which slowly solidifies to a paste and which contains 59.5% N-2-hydroxydodecyl-morpholine oxide and 1.2% N-2-hydroxydodecyl-morpholine in water.

EXAMPLE 11

Following the procedure of Example 10, the following 2hydroxyalkyl morpholine oxides are prepared from the corresponding 1,2-epoxyalkane (e.g. using 1,2-epoxynonane for making the hydroxynonyl-morpholine oxide). After crystallization as in Example 1, the product has the indicated melting point.

|  | m.p. |
|---|---|
| N-2-hydroxynonyl-morpholine oxide | 149–150° C. |
| N-2-hydroxyundecyl-morpholine oxide | 150.5–151.5° C. |
| N-2-hydroxytridecyl-morpholine oxide | 151–152° C. |
| N-2-hydroxytetradecyl-morpholine oxide | 151–152° C. |
| N-2-hydroxypentadecyl-morpholine oxide | 151–152° C. |
| N-2-hydroxyhexadecyl-morpholine oxide | 151–152° C. |
| N-2-hydroxyheptadecyl-morpholine oxide | 150–151° C. |

EXAMPLE 12

Another liquid detergent composition contains 23% of the sodium linear alkylbenzenesulfonate of Example 7, 13% of the ammonium salt of sulfated ethoxylated alkanol of Example 7, 5% of the N-2-hydroxydodecyl morpholine oxide (supplied as the paste of Esample 10) 5% of sodium xylenesulfonate (hydrotrope). The mixture is adjusted to a pH of 7.5 In a test of its dishwashing performance, it is found to wash considerably more plates (in water of 150 ppm hardness) before the foam disappears than an otherwise identical formulation containing 5% lauric/myristic monoethanolamide or 5% lauric/myristic diethanolamide in place of the material of Example 10. The clear point of the product is 32° F. in contrast to clear points of 44° F. and 52° F., respectively, of the two liquid formulations used for the comparisons.

EXAMPLE 13

0.25 g. of N-2-hydroxydodecyl-morpholine oxide is added to 25 cc. of distilled water at room temperature (25° C.) with continuous stirring. The material dissolves quickly. The temperature of the solution is raised slowly to 100° C. and then cooled in an ice bath. The solution is found to be clear; the dissolved material does not come out of solution until the temperature is reduced to 2° C. In contrast, in this test, N-2-hydroxydodecyl-diethanolamine oxide forms a cloudy mixture at the outset.

EXAMPLE 14

This Example illustrates a liquid detergent for use in the machine-washing of clothes in cool water.

A liquid detergent is prepared by mixing in the following order, at a temperature of 145°–180° F., 32.3 parts of water; 0.005 part of a non-ionic detergent which is a polyoxyethylated nonyl phenol (specifically a condensation product of 15 mols of ethylene oxide and 1 mol of nonyl phenol); and 1 part of a copolymer of vinylmethyl ether and maleic anhydride (Gantrez AN-908); under these conditions the anhydride ring of the copolymer opens, forming an acidic partial ester with the polyethoxylated nonyl phenol. There are then added 1.6 parts of an aqueous 45.4% solution of KOH; 0.69 part of sodium carboxymethylcellulose; 2 parts of a 10% aqueous dispersion of fluorescent brighteners; 1.7 parts of an aqueous 1% solution of blue dye (Polar Brilliant Blue); 0.12 part of an aqueous 0.5% solution of green dye (D & C Green No. 8); 8.56 part of aqueous sodium silicate of 43.5% concentration in which the $Na_2O:SiO_2$ mol ratio is 1:2.35); 10 parts of a nonionic detergent which is a polyoxyethylated alkyl phenol (specifically a condensation product of 10 mols of ethylene oxide and one mol of branched chain dodecyl phenol); 1 to 5 parts of N-hydroxydodecyl-morpholine oxide; and 41 parts of an aqueous 60% solution of tetrapotassium pyrophosphate, together with a small amount of perfume. The brighteners used in the above formulation include (a) 0.08 part of Geigy "Tinopal RBS-200%", a naphthotriazole stilbene sulfonate brightener, and (b) 0.12 part of another stilbene brightener bis (anilino diethanolamino s-triazinyl) stilbene disulfonic acid.

EXAMPLE 15 a. A shampoo composition is prepared by mixing 2 to 5% N-2-hydroxydodecyl-morpholine oxide, 10% triethanolammonium lauryl sulfate and, the balance, water.

b. In another shampoo composition there is used 10% of sodium monosulfate of ethoxylated lauryl alcohol (made with 3 to 4 mols of ethylene oxide per mol of lauryl alcohol) in place of the triethanolammonium lauryl sulfate.

c. Another shampoo composition contains 10% of triethanolamine oleate, 9% of N-2-hydroxydodecyl-morpholine oxide, and 1.6% of a cationic dispersing agent, oleyl dimethyl benzyl ammonium chloride and, the balance, water.

d. A shampoo composition, in gel form, contains 68% of an aqueous 41% solution of triethanolammonium lauryl sulfate; 6% sorbitol; 4% ethyl alcohol; 1.8% methyl cellulose, serving as a thickener; 5% lauric-myristic diethanolamide; 1% N-2-hydroxydodecyl-morpholine oxide; a small amount of formaldehyde as a preservative and the balance water. The pH is adjusted to 7.2, as by addition of triethanolamine.

While the invention finds it greatest utility in the embodiment in which the unsubstituted 2-hydroxyalkyl morpholine oxides are used, it is also within the broader scope of this invention to use long chain 3-hydroxyalkyl morpholine oxides (which may be made in the same way as the corresponding 2-hydroxyalkyl compounds, using the corresponding 1,3-oxetane in place of the 1,2-epoxide) and to use compounds in which there is a substituent such as lower alkyl (e.g. methyl, ethyl or propyl) on one or more of the carbon atoms of the morpholine ring, forming such compounds as N-(3-hydroxydodecyl) morpholine oxide or N-(2-hydroxyhexadecyl) 2-methylmorpholine oxide.

It is to be understood that the foregoing detailed description is merely given by way of illustration and that many variations may be made therein without departing from the spirit of the invention. The "Abstract" given above is merely for the convenience of searchers and is not to be given any weight in defining the scope of the invention.

What is claimed is:

1. An aqueous cosmetic composition intended for application to the skin in the form of a lotion, cream, gel or clear liquid containing a morpholine oxide of the formula

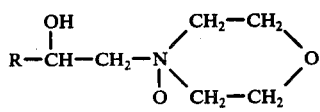

wherein R is alkyl of 6 to 20 carbon atoms.

2. A composition according to claim 1 which is in the form of a lotion containing one part by weight of said morpholine oxide and further includes a water-immiscible oily material selected from the group consisting of 1-3 parts by weight of mineral oil, 0.5-2 parts by weight of lanolin or lanolin alcohol, 1-3 parts by weight of $C_8$--$C_{18}$ fatty acids, 2-7 parts by weight of glyceryl $C_{18}$ fatty acid ester, and mixtures thereof.

3. A composition according to claim 1 wherein said composition is in the form of a lotion and contains an aqueous phase and oil phase in a ratio of about 5:1 to 20:1, said morpholine oxide is present in an amount of 0.2-5% by weight and is dissolved in said aqueous phase.

4. A composition according to claim 2 wherein said composition is a lotion and said oily material includes mineral oil.

5. A composition according to claim 3 wherein said oil phase includes mineral oil.

6. A composition according to claim 3 wherein said aqueous phase further includes a water-soluble synthetic organic detergent selected from the group consisting of anionic, nonionic, cationic and amphoteric detergents and mixtures thereof.

7. A composition according to claim 5 wherein said oily material is a mixture of, by weight, 1-3 parts of mineral oil, 0.5-2 parts of lanolin alcohol and 1-3 parts of $C_{18}$ fatty acid.

* * * * *